(12) United States Patent
Irianni

(10) Patent No.: US 9,220,690 B2
(45) Date of Patent: Dec. 29, 2015

(54) PATCH CONTAINING DICLOFENAC AND THIOCOLCHICOSIDE

(75) Inventor: Giuseppe Irianni, Episcopia (IT)

(73) Assignee: EPIFARMA SRL, Episcopia (PZ) (IT)

( * ) Notice: Subject to any disclaimer, the term of this patent is extended or adjusted under 35 U.S.C. 154(b) by 0 days.

(21) Appl. No.: 14/232,703

(22) PCT Filed: Jun. 15, 2012

(86) PCT No.: PCT/EP2012/061468
§ 371 (c)(1),
(2), (4) Date: Jan. 14, 2014

(87) PCT Pub. No.: WO2013/010737
PCT Pub. Date: Jan. 24, 2013

(65) Prior Publication Data
US 2014/0155342 A1    Jun. 5, 2014

(30) Foreign Application Priority Data
Jul. 20, 2011    (IT) .............................. MI2011A1355

(51) Int. Cl.
*A61K 9/70*    (2006.01)
*A61K 31/205*    (2006.01)
*A61K 31/704*    (2006.01)
*A61K 31/196*    (2006.01)

(52) U.S. Cl.
CPC ............. *A61K 9/7023* (2013.01); *A61K 9/7061* (2013.01); *A61K 31/196* (2013.01); *A61K 31/205* (2013.01); *A61K 31/704* (2013.01)

(58) Field of Classification Search
CPC . A61K 9/7061; A61K 31/196; A61K 31/704; A61K 31/205; A61K 9/7023; A61K 2300/00
See application file for complete search history.

(56) References Cited

U.S. PATENT DOCUMENTS

| 5,656,286 A * | 8/1997 | Miranda et al. ................ 424/449 |
| 6,063,399 A * | 5/2000 | Assmus et al. ................ 424/449 |
| 2011/0244023 A1* | 10/2011 | Cottrell et al. ................ 424/449 |

FOREIGN PATENT DOCUMENTS

| EP | 0965626 | 12/1999 |
| EP | 0837684 | 4/2002 |
| WO | 03055471 | 7/2003 |
| WO | 2008109018 | 9/2008 |

OTHER PUBLICATIONS

International Search Report issued in counterpart PCT Application No. PCT/EP2012/061468.
Written Opinion of International Searching Authority issued in counterpart PCT Application No. PCT/EP2012/061468.

* cited by examiner

*Primary Examiner* — Anoop Singh
*Assistant Examiner* — Doan Phan
(74) *Attorney, Agent, or Firm* — Silvia Salvadori, P.C.; Silvia Salvadori

(57) ABSTRACT

The present invention relates to a patch for the transdermal release of diclofenac or a pharmaceutically acceptable salt thereof, in particular diethylamine salt, and thiocolchicoside.

7 Claims, 2 Drawing Sheets

Figure 1:
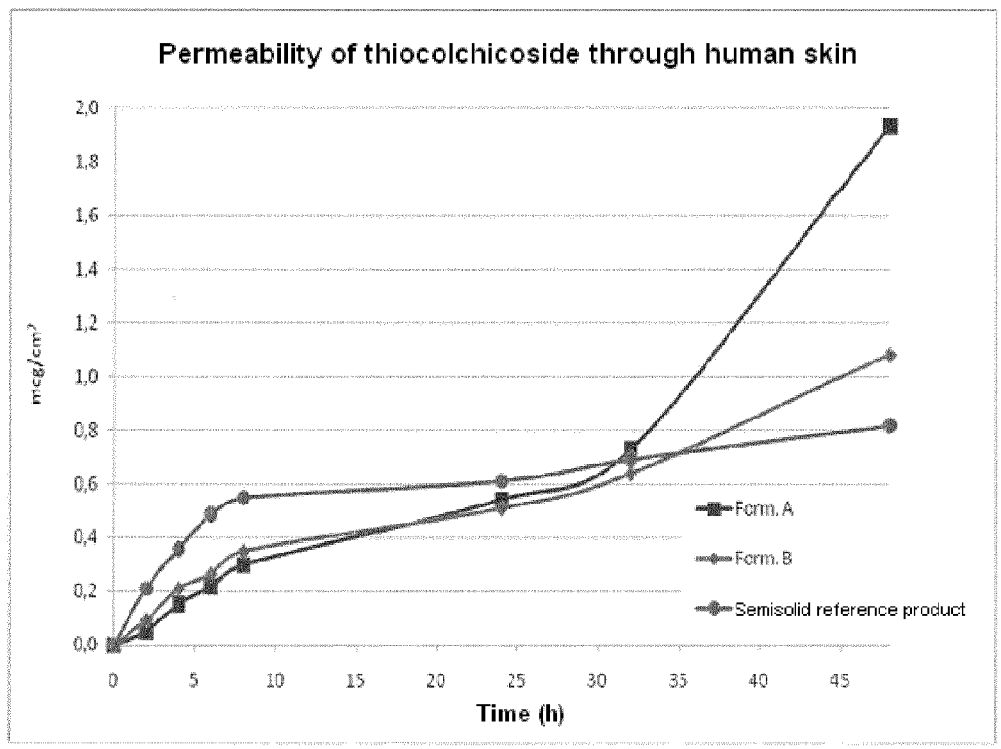

Thiocolchicoside flows:

Formulation A: 0,03 μg cm$^2$/h

Formulation B: 0,01 μg cm$^2$/h

Semisolid reference product: 0,01 μg cm$^2$/h

Diclofenac flows:

Formulation A: 1,09 µg cm²/h

Formulation B: 0,46 µg cm²/h

Reference patch: 0,73 µg cm²/h

PATCH CONTAINING DICLOFENAC AND THIOCOLCHICOSIDE

BACKGROUND TO THE INVENTION

This application is a U.S. national stage of PCT/EP2012/061468 filed on Jun. 15, 2012, which claims priority to and the benefit of Italian Application No. MI2011A001355 filed on Jul. 20, 2011, the contents of which are incorporated herein by reference in their entirety.

The present invention relates to a patch for the transdermal release of diclofenac or a pharmaceutically acceptable salt thereof, in particular diethylamine salt, and thiocolchicoside.

Numerous transdermal formulations in the form of adhesive patches able to release active ingredients of various kinds are known. This administration route is particularly indicated for non-steroidal anti-inflammatory drugs, especially when long-term treatments located in specific areas of the body are required. Transdermal administration reduces the risk of the side effects, especially at gastrointestinal level, which are sometimes encountered with these medicaments.

Diclofenac (2-(2-[2,6-dichlorophenylamino]phenyl)acetic acid) is one of the most widely used non-steroidal anti-inflammatory drugs due to its marked pharmacological activity.

Numerous formulations of diclofenac for topical application are known, in which it is present as sodium salt, potassium salt, diethylamine salt and hydroxyethylpyrrolidine salt in the form of a gel, patch or spray.

Transdermal formulations of diclofenac, in particular of its sodium salt, are disclosed, for example, in EP 524582, EP 582727, U.S. Pat. No. 6,193,996, EP 209975, JP 6056660, WO 99/03461, U.S. Pat. No. 4,999,379, and EP 965626.

Some of the formulations have been developed and are available on the market. Examples of said formations are a 60 g 1% gel with a recommended dose of 2-4 g 3-4 times a day for local treatment of rheumatic or traumatic pain and inflammation of the joints, muscles, tendons and ligaments, and a patch (FLECTOR TISSUGEL or DICLOREUM TISSUGEL) containing 180 mg of diclofenac hydroxyethylpyrrolidine salt to be administered twice a day for the treatment of peri-articular/tendinous inflammatory rheumatological disorders, whether isolated or occurring in the course of systemic disorders, or for the treatment of extra-articular inflammatory rheumatological disorders.

Thiocolchicoside, also known as 3-demethyl-thiocolchicine glucoside, is a glucoside extracted from the seeds of *Colchicum autumnale*, which possesses a muscle-relaxant, anti-inflammatory, analgesic and anaesthetic action. Examples of available formulations of thiocolchicoside are 30 g 0.25% creams and ointments which contain 250 mg of active ingredient per 100 g of cream, or 75 mg per tube, marketed under the name MUSCORIL. The indicated dose is 2-3 applications a day for the treatment of acute and chronic lumbosciatic pain, cervicobrachial neuralgia, refractory torticollis and post-traumatic and post-operative pain syndromes.

A combination of diclofenac sodium salt and thiocolchicoside in the form of an injectable solution is described in Minerva Anestesiologica, October 1991, pages 1084-1085.

Pharmaceutical compositions in solid form containing a diclofenac salt and thiocolchicoside are disclosed in EP 0 837 684 B1. Examples of the compositions described are tablets, capsules, topical gels and suppositories, wherein diclofenac is present as sodium salt. The compositions are suitable for immediate or controlled release of the active ingredients they contain.

DESCRIPTION OF THE INVENTION

It has now been discovered that the application of a patch containing diclofenac or a pharmaceutically acceptable salt thereof and thiocolchicoside allows the synergy between the two ingredients to be exploited optimally, and leads to greater therapeutic activity at lower doses than those obtainable by administering the two active ingredients separately or combined in other topical administration forms.

The subject of the present invention is therefore a patch containing, dispersed in an adhesive matrix, diclofenac or a pharmaceutically acceptable salt thereof, thiocolchicoside, and optionally excipients suitable for pharmaceutical use. In a preferred embodiment of the invention, the patch contains diclofenac in salt form with diethylamine.

In one embodiment of the invention, the patch consists of a film made of plastic or other material on which is distributed the adhesive matrix containing diclofenac or a pharmaceutically acceptable salt thereof, thiocolchicoside, and optionally excipients suitable for pharmaceutical use and a protective layer.

In a preferred embodiment of the invention, the adhesive matrix comprises:
- a copolymer of acrylic or methacrylic acid or its esters (component A);
- a cationic copolymer obtained by copolymerisation of dimethylamine ethylmethacrylate and neutral esters of methacrylic acid, such as methyl, ethyl and butyl esters (component B);
- a cationic copolymer obtained by copolymerisation of ethyl acrylate, methyl methacrylate and trimethylammonium ethyl-methacrylate (component C).

Copolymers of acrylic or methacrylic acid and its esters (component A) comprise poly(2-ethyl-hexyl acrylate-co-acrylic acid), poly(2-hydroxy ethyl acrylate-co-acrylic acid-co-methyl acrylate), poly(2-ethyl-hexyl acrylate-co-acrylic acid-co-methylacrylate), and poly(2-ethyl-hexyl acrylate-co-acrylic acid-co-butylacrylate-co-vinyl acetate).

Said copolymers are available on the market under the following names: Duro-Tak® (Henkel), MG-0607® (Dow Corning), Gelva® (UCB chemicals) and Luvimer® (BASF).

Further examples of acrylic or methacrylic acid copolymers suitable for the purposes of the invention are described in Satas, "Acrylic Adhesives," Handbook of Pressure-Sensitive Adhesive Technology, 2nd ed., pp. 396-456 (D. Satas, ed.), Van Nostrand Reinhold, New York (1989).

Component B is preferably the cationic copolymer obtained by copolymerisation of dimethylaminoethyl-methacrylate, butylmethacrylate and methyl methacrylate. Said copolymer is available on the market, one example being poly(butyl methacrylate-co-(2-dimethylaminoethyl) methacrylate-co-methyl methacrylate) copolymer 1:2:1 with CAS registry number 24938-16-7, marketed under the brands "Eudragit E 100" and "Eudragit E12.5".

Components A and B are present in the adhesive matrix in variable proportions, and the total quantity of the two components falls into the range of 50 to 90% of the weight of the dried adhesive matrix.

Component C can typically constitute 0.1 to 10%, preferably 0.1 to 5%, by weight of the total adhesive matrix. Said copolymer is available on the market, one example being poly(ethyl acrylate-co-methyl methacrylate-co-(2-trimethylammoniumethyl) methacrylate chloride) copolymer 1:2:0.2 with CAS registry number 33434-24-1, marketed under the brand "Eudragit RL100" or "Eudragit RL PO" (ammonium methacrylate copolymer).

Diclofenac is preferably present in the adhesive matrix as the salt of sodium, potassium, calcium, ammonium, ethylamine, diethylamine or N-(2-diethylamino)pyrrolidine. The salt with diethylamine is particularly preferred.

Diclofenac or its salt are preferably present in the adhesive matrix in quantities ranging between 1 and 15%, preferably between 5 and 10%, by weight of the total adhesive matrix.

Thiocolchicoside can be present in the composition in quantities ranging between 0.1 and 5% by weight of the total adhesive matrix.

In a preferred embodiment of the invention, the adhesive matrix contains diclofenac diethylamine salt in a quantity ranging between 5 and 10%, and thiocolchicoside in a quantity ranging between 0.1 and 1% by weight of the total adhesive matrix.

The adhesive matrix can also contain excipients such as stabilisers, solubilisers or substances designed to modify the release rate or increase the transdermal absorption of the active ingredients it contains.

The adhesive matrices present in the patch according to the present invention can be prepared by solubilising component B in a suitable organic solvent and then adding diclofenac or a pharmaceutically acceptable salt thereof and water.

After solubilisation, component A and component C with thiocolchicoside and any other excipients used are added under stirring.

The mixture thus obtained is spread on a suitable medium, such as a plastic film or silicone paper. The mixture on the medium is then stove-dried with forced ventilation at temperatures of between 40° C. and 120° C., preferably at 80° C. for 20 min.

After drying, the adhesive matrix is bonded to a suitable protective layer, such as a polypropylene film or a film made of fabric or synthetic non-woven fabric. The material is cut to form patches which are then packaged in sachets impermeable to gases and liquids.

A further subject of the invention is therefore a patch as defined above, also including a plastic film on which the adhesive matrix is distributed and a protective layer.

The quantitative compositions of four particularly preferred adhesive matrices according to the invention, expressed as percentages by weight of the dried product, are shown below by way of example (Tables 1-4).

TABLE 1

| Ingredients | % w/w |
| --- | --- |
| Diclofenac diethylamine salt | 8.13 |
| Thiocolchicoside | 0.50 |
| Durotak 87-2852 (component A) | 57.77 |
| Eudragit E100 (component B) | 7.00 |
| EuRL (component C) | 1.60 |
| PEG12 stearate | 15.00 |
| Sorbitan oleate | 5.00 |
| Propylene glycol | 5.00 |

TABLE 2

| Ingredients | % w/w |
| --- | --- |
| Diclofenac diethylamine salt | 8.13 |
| Thiocolchicoside | 0.50 |
| Durotak 87-2852 (component A) | 57.77 |
| Eudragit E100 (component B) | 7.00 |
| EuRL (component C) | 1.60 |
| PEG12 stearate | 16.50 |
| Sorbitan oleate | 5.50 |
| Isopropyl myristate | 3.00 |

TABLE 3

| Ingredients | % w/w |
| --- | --- |
| Diclofenac diethylamine salt | 13.94 |
| Thiocolchicoside | 1.00 |
| Durotak 87-2852 (component A) | 48.41 |
| Eudragit E100 (component B) | 11.00 |
| EuRL (component C) | 2.60 |
| Peg400 di-laurate | 13.05 |
| Sorbitan oleate | 5.00 |
| Lauric alcohol | 5.00 |

TABLE 4

| Ingredients | % w/w |
| --- | --- |
| Diclofenac diethylamine salt | 14.78 |
| Thiocolchicoside | 2.00 |
| Durotak 87-2852 (component A) | 51.48 |
| Eudragit E100 (component B) | 12.87 |
| EuRL (component C) | 4.72 |
| Peg400 mono-oleate | 8.55 |
| Span80 | 4.37 |
| Oleic acid | 1.23 |

A further aspect of the invention relates to the use of the patch described here for local treatment of rheumatic or traumatic pain and inflammation of the joints, muscles, tendons and ligaments, in particular for the treatment of articular and extra-articular inflammatory rheumatological disorders, acute and chronic lumbosciatic pain, cervical neuralgia, torticollis and post-traumatic and post-operative pain syndromes.

The examples below illustrate the invention in greater detail.

Example

Comparative Study

Diclofenac diethylammonium and thiocolchicoside were combined in a single formulation, and the dose of the two active ingredients was selected on the basis of in vitro experimental skin permeability tests using Franz diffusion cells. In these permeation experiments, a diclofenac sodium patch (containing 140 mg), already marketed and of proven efficacy, and a semisolid thiocolchicoside product containing 0.25% of active ingredient, were selected as reference. Skin permeability tests were conducted in vitro, by applying as donor phase a sample patch containing diclofenac sodium (1 mg/cm$^2$) with an area of 1.77 cm$^2$ and 100 mg of semisolid product containing thiocolchicoside on the same surface.

Diclofenac and thiocolchicoside flows comparable to those obtained from the commercial reference products were obtained by incorporating 7% and 0.5% of the respective active ingredients in the patch. Among the various absorption promoters, 3% isopropyl myristate (formulation A) and 5% propylene glycol (formulation B) proved particularly suitable.

Figure 2:
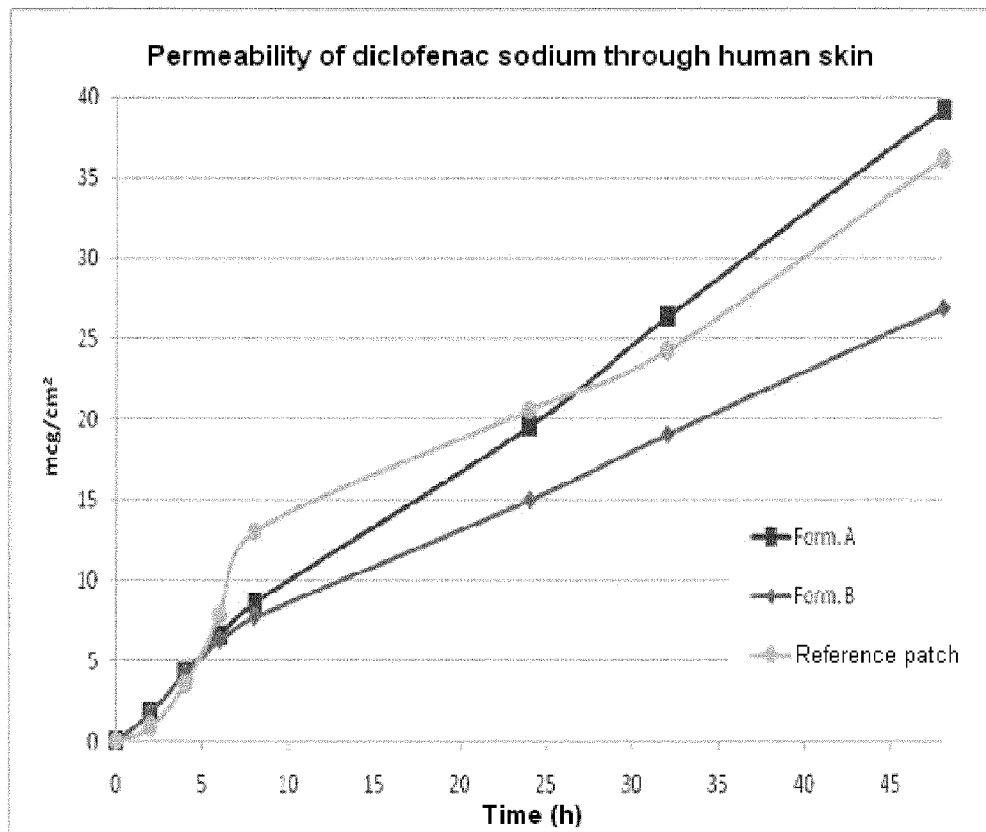

FIGS. 1 and 2 contain human skin permeation graphs for the two selected formulations under study and the reference products, with the corresponding flows.

On the basis of the results obtained, the thiocolchicoside and diclofenac flows obtained from formulations A and B can be deemed comparable to those obtained from the reference products.

The invention claimed is:

1. A patch containing, an adhesive matrix dispersed therein, diclofenac or a pharmaceutically acceptable salt thereof, thiocolchicoside and optionally pharmaceutically acceptable excipients, wherein
   (i) the adhesive matrix comprises component A as a copolymer of acrylic or methacrylic acid or its esters; component B as a cationic copolymer obtained by copolymerization of dimethylamionethyl-methacrylate and methacrylic acid neutral esters comprising methyl, ethyl and butyl esters; and component C as a cationic copolymer obtained by copolymerization of ethyl acrylate, methyl methacrylate and (trimethylammonium)methyl-methacrylate;
   (ii) the total quantity of components A and B in the adhesive matrix ranges from 50 to 90% of the total weight of the dried adhesive matrix; and
   (iii) component C is present in an amount ranging from 0.1 to 10% of the total weight of the dried adhesive matrix.

2. The patch according to claim 1, wherein diclofenac is in the form of diethylamine salt.

3. The patch according to claim 1, wherein diclofenac or a salt there of is in an amount ranging from 1 to 15% by weight of the total weight of the dried adhesive matrix and thiocolchicoside is present in an amount ranging from 0.1 to 5% by weight of the total weight of the dried adhesive matrix.

4. The patch according to claim 1, wherein diclofenac is present as diethyalmine salt in an amount ranging from 5 to 10% by weight of the total weight of the dried adhesive and thiocolchicoside is present in an amount ranging from 0.1 to 1% by weight of the total weight of the dried adhesive.

5. The patch according to claim 1, wherein the adhesive matrix also contains stabilizers or solubilizers.

6. A method of locally treating joint, muscle, tendon or ligament pain and inflammation of rheumatism or trauma in a subject in need thereof, the method comprising applying the patch of claim 1 to the skin of said subject.

7. The method according to claim 6, wherein said joint, muscle, tendon or ligament pain and inflammation of rheumatism or trauma is selected from the group consisting of articular and extra-articular rheumatic inflammatory disorders, acute and chronic lumbosciatic pain, cervical neuralgia, torticollis, and post-traumatic and post-surgical pain syndromes.

* * * * *